(12) United States Patent
Stack (10) Patent No.: US 8,951,046 B2
(45) Date of Patent: Feb. 10, 2015

(54) DESKTOP-BASED OPTO-COGNITIVE DEVICE AND SYSTEM FOR COGNITIVE ASSESSMENT

(75) Inventor: Matthew E. Stack, Boston, MA (US)

(73) Assignee: Sync-Think, Inc., Boston, MA (US)

( * ) Notice: Subject to any disclaimer, the term of this patent is extended or adjusted under 35 U.S.C. 154(b) by 109 days.

(21) Appl. No.: 13/507,991

(22) Filed: Aug. 10, 2012

(65) Prior Publication Data

US 2014/0046193 A1    Feb. 13, 2014

(51) Int. Cl.
*G09B 19/00* (2006.01)
(52) U.S. Cl.
USPC .......................................................... 434/236

(58) Field of Classification Search
USPC .................................. 351/206; 434/236–238
See application file for complete search history.

(56) References Cited

U.S. PATENT DOCUMENTS

| 7,390,091 | B2 * | 6/2008 | Clemons et al. | 351/245 |
| 2007/0236663 | A1 * | 10/2007 | Waldorf et al. | 351/206 |

* cited by examiner

*Primary Examiner* — Timothy A Musselman
(74) *Attorney, Agent, or Firm* — Morgan, Lewis & Bockius LLP (57) ABSTRACT

A highly portable desktop arrangement for cognitive testing which eliminates environmental effects is provided by a clam shell enclosure having a face mask on one face and housing a computer screen at an opposing wall, with accurate gaze direction measurement made by determining the position of the pupil if an individual whose face is pressed to the mask for eliminating head movement relative to the computer screen.

20 Claims, 7 Drawing Sheets

DESKTOP-BASED OPTO-COGNITIVE DEVICE AND SYSTEM FOR COGNITIVE ASSESSMENT

FIELD OF THE INVENTION

This invention relates to cognitive assessment and more particularly to the utilization of a moving dot and the perception thereof to provide accurate indications of cognitive ability.

BACKGROUND OF THE INVENTION

As indicated by U.S. Pat. Nos. 8,048,002; 7,819,818; 7,708,700; and 7,384,399, it is possible to measure cognitive ability by utilizing eye tracking techniques and the gaze direction of the eye to be able to detect cognitive impairment. In order to detect cognitive impairment, accurate measurements must be made of the gaze direction of the eye as it tracks the dot.

The problem with simply presenting the dot on a computer screen is first and foremost that environmental effects such as ambient light and distractions disturb the test subject when the test subject is looking at the screen.

The second problem has to do with the exact position of the test subject's head with respect to the dots on the screen and more particularly with respect to the cameras that are utilized in the eye tracking procedure.

Thirdly, there is a problem in the eye tracking procedure with the positioning of an LED light source to present a precisely positioned glint on the surface of the retina in which the glint is used as a reference point when measuring the gaze angle.

The fourth problem is that if one seeks to measure head position with respect to the screen, cameras or LED sources, then a large error is introduced in the gaze angle measurement. As a result, accurate measurement of the direction of the eye as it tracks the dot is very difficult. For instance, one needs accuracy to the sub pixel level to obtain accurate gaze angle measurement. However, head error swamps this accuracy because head position is only available to accuracies of 5 to 10 pixels. What is now presented is additional general background.

Eye Trackers

By way of general background, current state of the art eye trackers are distinguished from each other primarily via the physical layout of the devices and the relationship between the physical layout and how the patient or the test taker or the eye tracking device wearer interacts with the device. Existing eye trackers can be categorized into three main types of eye trackers: head mounted eye trackers, non-head mounted stationary eye trackers and applied-to-face eye trackers.

Head mounted eye trackers are typically affixed to the face or to the head via straps or latches and most often are attached either to glasses or as a helmet on top of the head. The cameras for the eye tracker and the associated optics and sources of illumination are then applied over or fixed on top of the helmet or glasses so that they are held by some feature of the head or face in a relatively stationary way relative to the location of the eyes. These eye trackers aim to reduce their weight, attempt to be as easy to put on and remove as possible, and are typically centered around lightweight electronics, such as cameras and optics, in order to reduce the amount of strain placed on the device wearer's neck. Variations on this device have included telescoping elements that stick out in front of the face or shallow facial mounted features that attempt to minimize the amount of angular torque generated on the neck by placing the optics as close to the eye as possible.

Sometimes, in an effort to reduce the weight of the head-mounted device, only the minimal amount of electronics and optics are placed on the head and the data is wirelessly transmitted to a secondary or tertiary unit or other unit that does the majority of the heavy duty processing. This strategy is employed often to save battery life of the device where it is assumed that the battery life is consumed because of the processing time and intensity of the algorithm's run on the images captured from the cameras of the head-mounted eye tracker. A significant amount of intellectual property is involved in reducing the weight and the complexity of these head-mounted devices and these design decisions are known in the prior art and described by their patents and other surveys of previous attempts and methods of designing head-mounted eye tracker devices.

Head-mounted eye trackers can be uncomfortable to wear, time consuming to install on the head and introduce sources of error intrinsic to their design including head drift, eye drift, and gaze drift. All of these errors derive from the movement of the head-mounted device on the head. In addition, due to their portability, the head-mounted eye trackers generally suffer from lower performance hardware and thus lower frame rates.

Non-head mounted stationary eye trackers are fixed, out-of-distance eye trackers. The majority of the electronics are mounted on the stationary location. For instance, on the dashboard or window of a car, on the desktop, on a laptop, front face of the monitor or screen or perhaps on a wall in a shopping mall. The point of the stationary eye tracker is to not involve any direct physical interaction with the patient. Instead, high-power illumination sources, for instance, infrared LED light sources are shown from a distance and algorithms are employed in order to distinguish infrared reflection on the surface of the eye, facial recognition, facial feature detection, and head direction and orientation. It is from this field of analysis that corneal reflection and gaze transformation-based analysis emerged as critical in order to eliminate the problem of detecting where the eyes were looking when the head could be in any number of different possible physical orientations. Thus, this type of eye tracking requires the use of high-power infrared point light sources and very accurate analog in-focus image generation to ensure that downstream computation and analytical processes have the highest quality input source possible since the input source of the eyes are assumed to be at a further distance of a location than if the cameras were located directly in front of the eye.

As non-head mounted stationary eye trackers do not have the requirement for portability and power conservation that head-mounted eye trackers have, as they are typically stationary and therefore able to draw from outlet wall supply sources. However, the environment is noisier in which they are being applied, which requires more computational power to be expended in accurately detecting the face, location of the eyes. Oftentimes extensive calibration is required in order to determine whether the eyes are being detected correctly and that the patient has the right configuration and the right angle of the head. These devices often are characterized by having configurations of anywhere between half an hour to an hour or more of pre-configuration and configuration time before settling in on the proper configuration.

Applied-to-face eye trackers are a relatively newer form of eye trackers where the user holds the device or eye tracker relative to their head or face in closer proximity than a non-head mounted stationary eye tracker, but not necessarily as close as a head-mounted eye tracker. For instance, cellular phones with high-power cameras can be used as a platform to be an applied-to-face eye tracker by which the user can hold the camera close to the eye. This eye tracker category suffers the problems of motion and mechanical-based variability introduced by the subject holding the device and the optics with non-steady hands. Therefore, significant analytical work is then applied downstream in order to eliminate shaking variation or variability to get to only the features of the eye that one is trying to extract from the eye tracker.

Applied-to-face eye trackers are typically easy to use, portable, highly interactive, user friendly and relatively straightforward and simple to apply. However, they suffer from extremely low performance. They tend to introduce their own sources of noise when used outside of their intended lower-end applications. Another problem is that they are very reliant on the user for a significant amount of calibration, interaction elements and data.

It is also important to mention that in the current state of the art of eye trackers, few eye-tracking devices used for cognitive assessment, if any, is purpose-built and optimized from the ground up for opto-cognitive analysis. Eye trackers are typically designed for other purposes such as automated control graphical user interface navigation, consumer feedback testing, marketing assessment and efficiency studies and medical ophthalmological testing and evaluation. Thus, these eye trackers are optimized for the task at hand and designed for their primary task in their field, which do not match the design requirements necessary to be optimal for cognitive assessment, analysis and diagnostics.

Another drawback of the current state of the art of eye trackers is that despite the low cost of cameras, the cost of these eye trackers are tremendously high, especially for the head-mounted and non-head mounted stationary eye trackers. For head-mounted eye trackers, this is because of the amount of technology involved with isolating the controlled environment. For non-head mounted stationary eye trackers, this is due to the amount of technology involved in processing the data from the cameras to account for the high environmental noise. Applied-to-face eye tracker devices tend to use lower quality cameras, so the argument is shifted lower on the cost scale, but they also tend to include other features in the general-purpose devices and so the cameras don't get the full share of the value of the technology cost placed into the device.

Cognitive optical eye tracking has a unique requirement above that of normal eye tracking. It requires the high degree of precision and accuracy that head-mounted eye trackers typically require, the degree of interactivity between the user and the device that non-head mounted stationary eye trackers provide, and the relative ease of use and user friendliness that applied-to-face eye trackers provide. They also need to have a controlled environment and have some degree of portability. The device does not need to be pocket size, but they do need to be portable enough to be moveable from one location to another by a single person in a relatively reasonably short period of time.

The ideal cognitive eye tracker should also recognize that the cost of the camera relative to the cost of the technology is quite low. The ideal cognitive eye tracker places the majority of the emphasis of the cost of building materials on the cameras and minimize, if possible, the cost of all other components of the technology to deliver the highest possible ratio between camera cost and the end-device cost. This objective is an economic objective, and not necessarily a technological objective, but if the field of optical cognitive research is to expand, this ratio has to be amplified, recognized and encouraged by technological solutions proposed in the field. The problem with the current eye tracking technology is therefore the fact that much more emphasis is placed on the configuration of the device relative to the head and the face than the effect of the cameras. The effect of the cameras are almost minimized to the point where the cameras could almost be any replaceable camera and the technology cost is higher on the optics and the illumination sources that surround the basic eye tracker cameras.

Eye Tracking Methods

In the field of eye tracking, one important distinction is which technology the eye tracker utilizes to track the eyes, whether the eye tracker employs what is known as dark pupil or light pupil analysis. The terms dark pupil and light pupil refer to the image and appearance of the pupil in the images taken by the cameras that are looking at the eye when infrared LED light is shone into the eyes. Infrared LED light is the most common source of light used to illuminate the eye because it does not conflict or interfere with the visual light spectrum.

The dark pupil eye tracking method involves shining the infrared LED light into the eye at an angle so that the light is absorbed primarily by the walls of the inside of the eye and thus not reflected outwards, which allows the infrared LED light that shines on the white of the eye to reflect back. The eye then appears to be white where the white of the eye is and a dark center where the pupil is. The infrared LED light places a dot-like glint on the surface of the eye and the glint location is used to determine the location of the pupil for tracking the eyes.

The white pupil eye tracking method in comparison shines the infrared LED light directly into the front of the eye, which then bounces off the back of the eye and emit or project itself back out the front of the eye. This will then swamp the amount of infrared LED light that is reflecting off the surface of the eye and cause the pupil to appear as a bright white circle. Thus there will typically be two different intensities of white light. One of the intensities of white light is that reflected directly off of the surface of the eye, which can be brighter or dimmer than that second set of light that was reflected into the eye and back out. Analysis involved in distinguishing the light that is coming from the reflective pupil versus the light that is reflecting directly off the front surface of the white pupil is known as white pupil eye tracking.

There are advantages and disadvantages for both methods. While it was thought that white pupil tracking is more precise and accurate, dark pupil tracking requires a less complex analysis and a simpler environmental setup in order to track the eyes with this method.

SUMMARY OF INVENTION

In order to solve the above-mentioned problems for accurate eye tracking and therefore the ability to achieve significant cognitive impairment results while at the same time providing significant portability and cost reduction, in the subject invention a typical laptop computer with a screen is placed in an enclosure which has at its proximal end a mask that positions the individual's face relative to the enclosure and thus to various components within the enclosure. It has been found that one of the more difficult requirements in looking at a computer screen is to make sure that a normal to the face is normal to the plane of the screen. If this can be established, then a simple system, which measures pupil position, can be used without any calibration whatsoever. By providing a mask which positions the face normal to a screen, one can utilize a more accurate technique for determining gaze position, that being the recognition of the position of the pupil as opposed to corneal reflection techniques.

The reason that it is possible to detect pupil position is that a red LED is made to tangentially illuminate the eye to pop out the pupil against the background so that the exact position of the pupil can be determined. Note this does not involve any critical alignment procedures. More particularly, if one illuminates the eye from an angle the light reflected by the surface of the eye will in general be detected as a white area, whereas the light that is reflected through the pupil will be dark. Therefore the position of the pupil is determined by the highly defined circumference of the pupil vis a vis the adjacent white area.

The subject mask is provided with cameras located beneath the eye and LED illuminators to one side or the other of the eye to permit pupil tracking which in turn permits exceedingly accurate gaze direction calculations using low cost off-the-shelf computers and an enclosure which is both low cost and portable. Also low cost cameras may be used because the requirement for precision high cost cameras is eliminated.

Another feature of the subject enclosure is that handholds are provided at the sides of the enclosure so that the test subject can press his face to the mask. Handholds are important because the motion of the head, especially when leaning over, is significant when using a mask to which the individual is supposed to press his face. The movement of the head magnifies head wobble that adversely affects the accuracy of the cognitive impairment measurement.

In the subject invention handholds are provided to either side of the enclosure so that an individual can press his head firmly to the mask and prevent head wobbling.

It will be appreciated that the subject invention envisions the use of standard laptops and it is therefore important that the mask position the individual's eyes no less than 38 centimeters from the laptop screen or more than 42 centimeters. If the individual's eyes are positioned less than 38 centimeters from the screen the individual may need to refocus his or her eyes in a nearsighted manner, in order to focus on the dot on the screen, resulting in his or her pupils to moving inwards toward the nose, in a cross-eyed manner. Also people who are far-sighted cannot see the dot clearly on the screen less than 38 centimeters from their eyes.

On the other hand, if the screen is more than 42 centimeters from the eyes of the test subject the lateral sweep angle for a moving dot is too small. This is a problem because to measure cognitive impairment with maximum accuracy, it is crucial to have the dot move as much as possible laterally in either direction respect to the test subject's field of view. Thus, if the lateral sweep angle is limited, the accuracy of the cognitive impairment measurement suffers.

More particularly, if the screen is too close to the individual, the dot will appear blurry. Likewise, if the screen is too far from the eyes of the individual, the dot may be less distinct due to the rods and cones in the retina lacking enough resolution to distinguish objects in the distance.

The result of the subject invention is that a highly portable desktop arrangement for cognitive testing is provided in which environmental effects are eliminated and in which increased accuracy gaze direction measurement is provided by the ability to track the pupil as opposed to iris position and corneal reflection gaze estimation systems.

As one further feature of the subject system, two screens are not necessary to perform the cognitive impairment measurement, one for the test taker and the other for the test administrator. It will be appreciated that in the prior art in eye tracking, multi-dot and extensive calibration is needed in order to ensure the performance of an eye tracker. For such calibration purposes a separate screen needed to be provided for the test administrator to be able to calibrate the system. However due to the fact that one can track the pupil as opposed to irises and glints, there is no calibration necessary. Therefore one need not have a second screen for the test administrator.

More particularly, in one embodiment, the subject system is a cognitive optical eye tracker that is a small, cube-like sized device that sits on the desk of a physician or a consumer's workspace and provides only the minimal amount of hardware required to place a set of cameras in front of the eyes in a dark pupil environment.

This desktop-based opto-cognitive device takes into account the fact that most experimenters and researchers will already have a computing device, such as a laptop in their possession. Therefore, instead of replicating additional unnecessary hardware to create an effective secondary system inside the eye tracker itself, this system is designed to be opened and closed like a clamshell design. When opened, a computing device, such as a laptop, can be inserted inside the device. The laptop is then configured and connected to the cameras via standard interfaces available such as USB, FireWire, high-speed serial, Ethernet, etc, and runs the eye tracking software and code that is optimized specifically to run on a laptop.

The subject device consists of two major hardware components. The first hardware component is the base of the device and the second hardware component is the top clamshell of the device.

The base of the device provides adequate support and structure for the device so that it can be mounted on a desk or flat working surface to ensure the device has minimal amount of slippage or movement on the surface or tabletop. The base of the unit serves as a platform onto which a laptop can be placed on inside the device when the top shell is opened. The base of the device contains slits along the sides and the back of the unit in order for cables and connectors to be attached to the laptop including power or peripherals. Two of these peripherals include the cameras themselves, which are attached directly to the mask. These slits are placed parallel to the surface of the table and relatively low on the base component of the device in order to allow for the cables to be as close to the bottom of the device as possible, which minimizes the amount of width of the device or depth of the device. Normally, the device would have to be large enough to include the lengthy, rigid cable connectors, which is true with most connectors today, causing the cable to extend an inch-and-a-half or two, or more beyond the edge of the laptop. Since the goal of the enclosure of the device is to fully isolate the laptop from outside noise and light sources, the device has to be large enough to encapsulate the entire laptop. Without the slits on the side of the base, the device would have to be wide enough to encapsulate the rigid extenders of the extended standard interface connector cables in addition to the laptop itself. With the slits present, the standard interface connector cables or the power connectors that come with the laptops can be passed through the slits and then connected into the laptop, and so the overall device size only has to be a small margin wider and deeper than the average laptop expected to be used in the device.

The slits on the edges of the base of the device are made out of rubber, or otherwise flexible material that provides a curtain effect, so that the cables can be passed through the slits and the curtain can be applied on top of the cabling. The curtain effect then will effectively serve to block off any additional and remaining light to seep into the dark enclosure.

The top clamshell of the device is attached to the base via a hinge mechanism, allowing the top clamshell to open and close. The top clamshell folds up and opens substantially back, allowing for the user to place the laptop inside onto the base of the device.

The top clam shell section of the device includes a number of components that are essential to the interaction and use of the device, specifically the sides of which include handholds for the user to place their fingers and to hold the device in a stationary manner with their arms bent and the elbow resting on the tabletop surface during the test taking procedure. This design makes the device easy to use and intuitively easy to interact with as the user's first inclination will be to reach for the purposely cut-out handholds and finger slots on the sides of the device, which are positioned roughly at the same location that their bent elbows would place their hands into at that height.

The handholds are a very important component of the top clamshell. Other eye tracking devices typically do not have handholds and therefore suffer from calibration errors because the users during the process of taking the test cannot control the relative location of where the head is positioned relative to the cameras. The handholds serve as an aesthetically obvious and intuitive place for the test taker place their hands to hold the device stationary while taking the test.

Another important feature of the top clam shell is the front faceplate. The front faceplate refers to the side of the packaging device facing the patient or the test taker, which also includes the section that contains a facemask built into and shaped into the side and the front face of the device. The position of the facemask is set to approximately two-thirds up from the bottom of the faceplate, which when taking into account the height of the device amounts to the median expected location where most adolescent and adults would feel comfortable placing their hand into the device when leaning forward onto the tabletop and onto their elbows. The specific height and location of the facemask is dictated by a formula or function that relates the size of the overall device. This is mostly driven by the size of the laptop that the device is designed to accommodate, along with the expected size and height of where the eyes will be placed. The latter is important as when looking into the device through the faceplate, the line from the eye gaze point to the surface of the laptop screen inside the device needs to be roughly at a 90-degree angle. This also means that the surface and face of the laptop must be slightly bent backwards, and this is accommodated for by fixing the laptop screen in place by a slight backward-facing ribbing component that is optionally built into the back wall of the device enclosure. The ribbing component at the back wall and the fixed eye mask of the faceplate also provides a fixed distance between the eyes and the screen.

The shape of the eye mask portion of the faceplate on the top clamshell of the device is designed for a comfortable, universal fit for any adult face, regardless of age, gender or ethnicity. The shape of the mask was designed by taking a 90% percentile average of reported face measurements across the population demographic between the ages of 8 and 20. The design for the universal eye mask shape was concentrated to three key face areas: cheekbones, nose bridge and forehead. These three key face areas were chosen as a pinpoint because they are the three areas of the face that has the least fat deposit and variation in fat deposits on one's face is the main cause for variation from one adult face to another. The eye mask's curvature tightly hugs the cheekbones, forehead and the side of the face to create a tight barrier, which blocks outside light from entering the enclosure of the device.

The placement of the hinge mechanism that connects the top clam shell to the base of the device is another important component of the design of the device enclosure. It is important that the hinge mechanism is placed relatively at the center of the middle edge of the device so that when the top hinged section is opened and pulled back, it does not require the device to be twice as deep to accommodate the fully unhinged top shell. Thus, this design decision makes the overall device smaller in profile when inserting and removing the laptop from inside the device enclosure.

The design of this device is specifically designed to fulfill the ideal eye tracker requirements for cognitive assessment. The device is designed to maximize the user friendliness of the interface and to be the most logical possible device for patients and experimenters and consumers to interact with. Great pain and care has been taken to make the device as obvious as possible for where the interaction between the device and the user will take place, for instance, placing handholds where hands should go and highlighting in specific colors where the face should go in addition to the face-conforming faceplate design. This altogether increases the aesthetic appearance of the device and simplifies the user interface.

Furthermore, the laptop enclosure design that creates a dark box effect, which creates a stable isolated environment with minimal external sources of light or environmental noise from the outside of the device, which could cause to introduce light rays or reflections inside the device that might negatively affect the eye tracking algorithm. For example, if the light leaked into the device reflects off the screen into the pupil of the test taker's eyes, it will create additional glints or affect the features on the surface of the eye unnecessarily. As a result, eye tracking would be made more difficult and make the eye tracker device less precise.

The subject device also solves the problem of high cost of the current state of the art of eye trackers for cognitive assessment. Unlike the current state of cognitive eye trackers, the invention is based on the technology for computability on readily available and low-cost computing devices that most households already have such as laptop and tablet computers. These are placed inside of the device where the screen of the tablet or laptop is the testing screen, thereby eliminating the need to have a dedicated embedded system display and screen. The device also takes advantage of the fact that the high-quantity production scale and the relative pervasiveness of laptops and tablet computers have driven the per-device cost down for that technology which has effectively made laptop and tablet computers the cheapest way to get a combined high performance processor, low-power drain and high-performance screen in one single package. Thus, the need to develop custom embedded electronics that achieve low power, high-performance computation and high-performance screen in a single device by using off-the-shelf components wrapped in a package designed to provide the opto-cognitive conditions of high-performance eye tracking testing is eliminated. Finally, the packaging itself is a relatively low cost as the primary component. What drives the cost down one high-low speed low-performance cameras that are attached via a common interface, such as USB, that is available in the consumer market. With the direct connection between the camera and the laptop, the image processing signals do not have to be routed through multiple tiers of custom hardware and image processing hardware being it can be applied to the algorithm to generate useful analytical data. Therefore, the cost of the electronic and the physical device is minimized to nearly the cost of cameras, cables and the mechanical design associated with housing those cameras.

This invention takes advantage of the existing hardware, computational ability of laptops, which when compared to the most of today's embedded hardware are either at least as good or often vastly superior to the current state of the art of embedded systems. This is because computing devices such as laptops and tablets are produced in such high scale that the scale has allowed manufacturers to take advantage of more efficient lower costs and sourcing and procuring high-performance processors and longer-lasting batteries as mentioned previously. The use of laptops also cuts out the need to do external desktop-based custom graphic cards and capabilities. Embedded system limitations too no longer apply, such as memory constraints, and the dynamic memory allocation capabilities of laptops can be utilized for instantaneous caching at a higher speed, which allows for dynamic feedback-based testing.

Furthermore, the device design minimizes most major sources of error. The shape of the device allows for a straightforward and intuitive interaction with the device, minimizes user error, test administrator error and other forms of user-interface noise that introduce error to the data file and thereby decrease the quality of the analysis performed for the opto-cognitive testing.

Although the subject invention focuses on the use of a laptop or a personal computer as a portable device that can be inserted inside the enclosure of the desktop unit, another embodiment of this invention includes a screen or a portable tablet that could be propped up in the back of the device enclosure to present the user and the test taker with an angled screen upon which the test is administered.

In the case of a computer screen or a monitor, the personal computer logic would be contained outside of the enclosure, unlike the laptop where the personal computer logic is contained at the base of the screen on the laptop.

In the case of a tablet, the tablet computer might have a built-in processing system that would permit it to do the processing of the standard interface connector cameras or the high-speed cameras connected to it in the one scenario. In another scenario, it might be that the tablet is lower performance, lower cost, and limited in capability and instead would require the processing functions of a desktop or laptop computer attached nearby or accessible over the internet, cloud hosting, some type of remote protocol or some wireless protocol. In each of these cases, the tablet serves mostly as a screen with some lightweight control interface and the rest of the control interfaces in processing is externalized from the laptop to another unit or a third party unit. However, this does not exclude the fact that some tablet computers are high performance enough to connect the standard interface connector cameras directly to them in order to conduct the test.

Inside the desktop-based enclosure, is some type of mechanism that is primarily mechanical or adhesive that connects the laptop screen backing or tablet to the back wall surface of the enclosure in order to keep it stationary relative to the position of the eyes looking through the faceplate. This is to ensure the appropriate angle and distance is preserved between the eyes and the surface of the screen, which has to be normal and the same throughout the duration of the test. Otherwise, this can disturb the test quality output and introduce a source of error that has to be accounted for during processing of the data file, in which the algorithm to do so in itself can introduce error and affect the test output. In addition, drift or head drift, the most common source of error, which is where the center point of the head with respect to the goggles drifts relative to the position of the tablet, can happen. This happens due to the movement of the head of the test taker, but it could also happen if the tablet was not secured to the back of the enclosure and drifted to the left or right over time.

BRIEF DESCRIPTION OF DRAWINGS

These and other features of the subject invention will be better understood in connection with the detailed description in conjunction with the drawings of which.

DETAILED DESCRIPTION OF DRAWINGS

Figure 1:
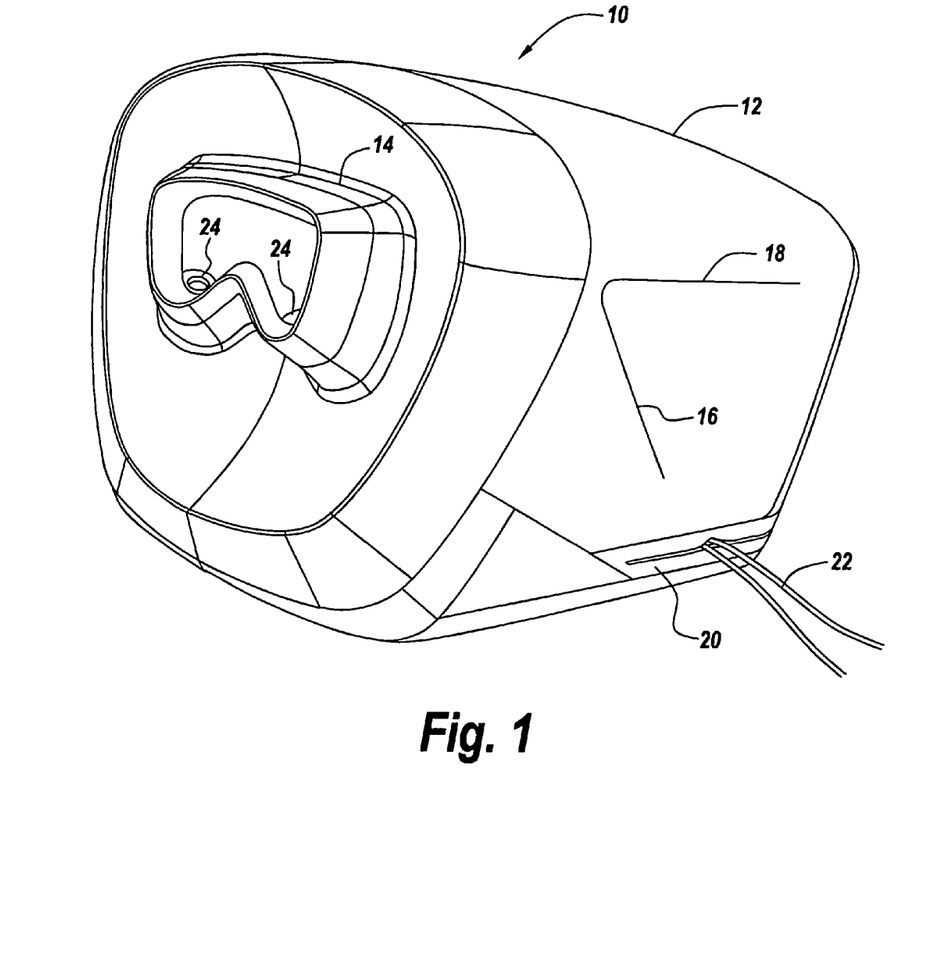
FIG. 1 is a diagrammatic illustration of an enclosure and mask for use in a desktop opto-cognitive device for cognitive assessment.

Referring now to FIG. 1, a desktop based opto-cognitive device 10 is provided with an enclosure 12 that has a mask 13 on its proximal face to which an individual taking a cognitive test is asked to press his or her face. It will be noted that the enclosure includes an integral angled handhold portion 16 as well as a horizontally orientated integral handhold portion 18, which is usable by the individual taking the test to press his or her face into mask 14 when the enclosure is supported on a pedestal at eye level. The enclosure also has a slit 20 to enable cabling 22 to pass from the outside of the enclosure to the inside of the enclosure to attach to an internally carried screen of a computing device, such as a laptop, personal computer or a tablet device.

As can be seen mask 14 includes cameras 24 located below the nose bridge of the mask with the camera and pointed towards the eyes of an individual taking the cognitive test to measure cognitive performance. Cognitive performance is ascertained by measuring gaze detection by detecting the position of the individual's pupils as they trail a moving dot on the screen.

Figure 2:
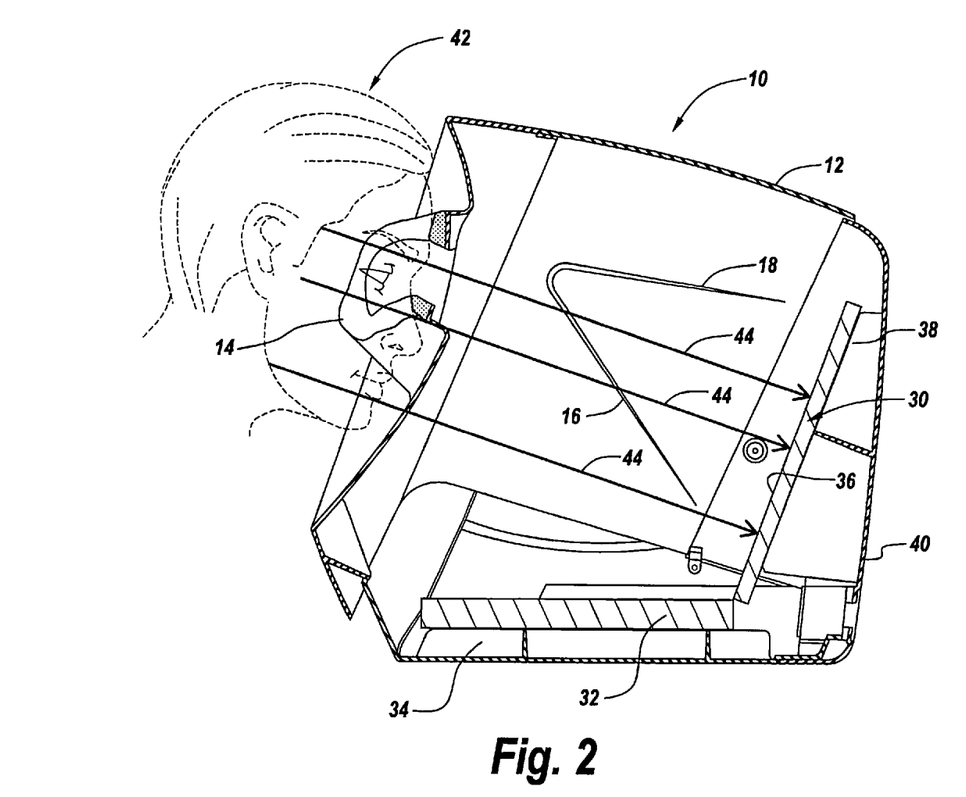
FIG. 2 is a diagrammatic illustration of the enclosure of FIG. 1, illustrating an individual having his or her face pressed to a mask which positions the eyes of the individual with respect to the screen of a laptop contained within the enclosure, thus to establish not only a fixed distance of the eyes to the screen but also that the plane of the screen is parallel to the plane across the individual's eyes such that the line of sight from the eyes to the screen is perpendicular to the plane of the screen.

Referring now to FIG. 2, enclosure 10 is provided in one embodiment with a laptop generally indicated by reference character 30 having a base 32, which rests on a support rib 34 at the base of the enclosure 12. The angled screen 36 of laptop 30 resting on a rib 38 attached to the back wall 30 of enclosure 12 to support the screen not only in its angled orientation with respect to its own base, but also, as will be discussed hereinafter to provide a plane for the screen that can be maintained perpendicular to a line from the individual's eyes to the screen, here shown in dotted outline at 42. The line of sight from the individual to the screen is indicated by arrows 44 to show that the plane of the eyes of the individual is maintained parallel to plane of the screen.

Also shown are handles 16 and 18, which in one embodiment are indents into the surface of the enclosure as illustrated in FIG. 1.

Figure 3:
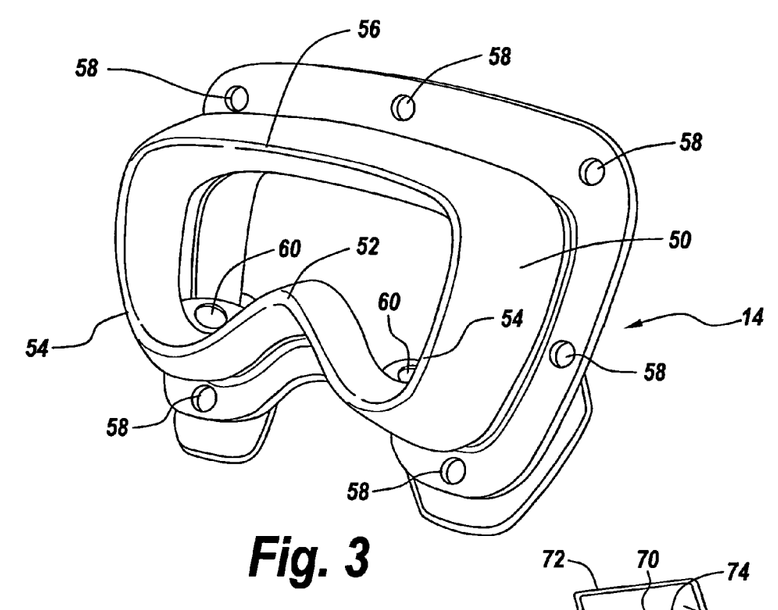
FIG. 3 is a diagrammatic illustration of a mask usable for the enclosure of FIG. 1, illustrating apertures through which cameras are adapted to protrude to measure pupil position and thus eye gaze direction.

Referring now to FIG. 3, mask 14 is shown to have an elastic rubberized mask material 50 which has a nose bridge 52 and cheeks support sides 54 as well as a forehead supporting portion 56 all of which forming a type of goggle. However, rather than being head worn, the goggles are mounted to the subject enclosure as for instance through bolt holes 58.

Also shown in this figure are apertures 60 which are adapted to house cameras pointing up towards the eyes of an individual when the individual has his head pressed to the mask, the purpose of which are to detect pupil position and thus gaze direction of the individual taking the cognitive test. Here it is to be noted that since the individual's head is immobilized with respect to the screen, a rather inexpensive single camera can be used to detect pupil position, as opposed to the rather 80 plus treated cameras used to detect gaze direction using glint detection and iris position.

Mask 14 has a number of features that make it universal and capable of fitting to any adult face, regardless of ethnicity or gender to provide a fixed distance between the eyes and the screen, and also between the eyes and the LED light sources used to provide the glints.

First, the mask is made from a compound foam that is non-compressible, yet comfortable. In one embodiment the foam is a polyurethane foam model PG 250 made by Spectrum Plastics Group of Westminster Colo., with the foam having a 55 shore hardness. The shape of the mask was designed by taking an average of reported face measurements across the population demographic in the 90% percentile between the ages of 8 and 20, and thus allows for a universal fit.

Secondly, the curvature of the forehead-contacting portion of mask 14 has a horizontal curvature of a radius of 79 mm at the bottom, closer to the eyes, and narrows to the top of the forehead of the mask, with a vertical curvature of a radius of 107 mm. The forehead-contacting portion of mask 14 is 165 mm wide at the bottom and 155 mm wide at the top with such measurements used to accommodate a wide variety of forehead widths and shapes.

Thirdly, the nose cutout has a nose depth of 60 mm and nose width of 90 mm, designed to accommodate even the longest and widest of noses.

Finally, the portion of the mask that engages the cheekbones was sized to give the IR LEDs enough depth in front of the eyes. Note that the cheekbone of the mask refers to a narrow horizontal cheekbone plate.

The above establishes a predetermined distance between the LEDs and respective eyeballs so that this distance is the same for all faces.

The mask when properly configured properly contacts the forehead and the cheekbones and creates a light tight barrier to outside light so that the mask surrounds the face with a light-tight seal. The curvature of the mask horizontally across the eye portion has a radius of 277 mm and a width of 200 mm, which assists with this light-tight seal.

As mentioned above, the design for the universal eye mask shape is concentrated on three key face areas, namely the cheekbones, the nose bridge and the forehead. These three key face areas are chosen as a pinpoint because they are the areas of the face that have the least fat deposit and variations in fat deposits on one's face is the main cause for variation from one adult face to another. The result is the facemask curvature tightly hugs the cheekbones, forehead and sides of the face to create a tight barrier, which blocks outside light from entering the enclosure of the device.

It is a feature of the subject invention that with a computing device such as a standard laptop placed on the ribs is shown in FIG. 2, the individual's eyes are no less than 38 centimeters from the laptop screen, nor more than 42 centimeters.

Figure 4:
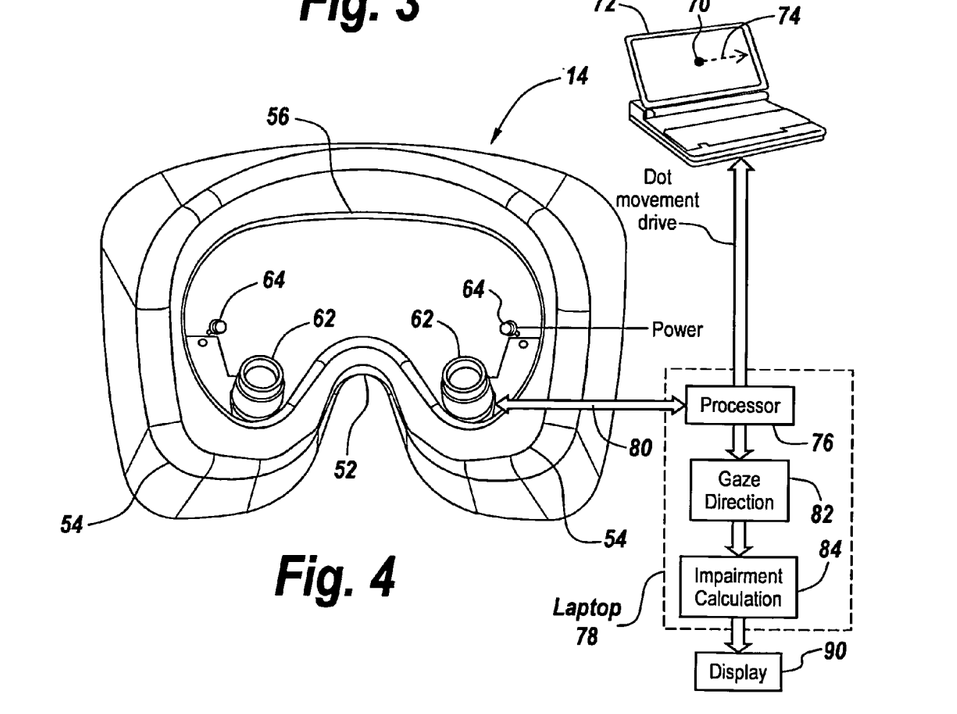
FIG. 4 is a diagrammatic illustration of the mask of FIG. 3 showing the mask-mounted cameras along with a processor, and a gaze direction and impairment calculation module for measuring cognitive function.

Referring to FIG. 4, mask 14 of FIG. 3 is shown in which like elements carry like reference characters and in which relatively inexpensive cameras 62 can be mounted into the orifices of 60 of FIG. 3 such that the cameras point upwardly towards an individual's eyes when the individual's face is pressed to the mask. Also shown are LEDs 64, the purpose of which is to shine a tangential light onto the eye so as to pop out the position of the pupil while at the same time illuminating the remaining part of the eye which appears white as opposed to the dark pupil.

When a moving dot 70 is placed on a computer screen 72 and is moved for instance as illustrated by dotted line 74, this movement is reflected in a change in the gaze direction of the individual taking the test. In order to obtain the gaze direction processor 76 within laptop 78 is utilized, with the output of the cameras as illustrated at 80 to detect gaze direction as illustrated at 82 in terms of the position of the pupil as detected by cameras 62. However, as illustrated at 84 cognitive abilities, or in fact cognitive impairment, may be ascertained in terms of the ability of the eye to track dot 70 as it moves. Also as illustrated in FIG. 4 the results of the cognitive impairment calculation may be displayed separately by a display 90. How gaze direction is detected in terms of pupil position measurement is as follows.

The processor and processing stage of calculation takes as an input the image of the eye and especially the dark pupil that is generated by the cameras and the infrared setup imbedded in the lower part of the face mask. The picture data is represented in pixels and the format can be anything from a raw picture to a compressed picture. The data input is specifically bounded in rectangular format such that the coordinates and position of the dark pupil appear roughly in the middle of the picture. The infrared LED illuminates the surface of the eye and also reflects into the dark pupil but not out, causing the dark pupil effect. The dark pupil effect is known in the literature and is described in the prior art as a method of eye tracking that is distinct from light pupil where the infrared LED is shown directly into the eye such that it bounces back out and illuminates itself in the form of white infrared light.

Once the pictures are generated by the cameras, these pictures are then stored to a data structure, which usually takes the form of a compressed movie or series/sequence of images. These images are stored to disk, or memory or random access memory for access by the processor and the software running on the processor.

The processor then performs a set of processing stages whereby it filters out the picture to determine where the dark pupil is in the picture. This is typically represented by a circular form of dark pixels with a hard circular ellipse edge. The ellipse edge is usually adjacent to the iris, which is either lighter colored or at least a greyer scale. In any event it is not dark or black, like the center of the pupil. Once the dark pupil pixel filter is applied, there is usually one large patch of dark pixels but also several smaller areas of dark pixels caused by for instance darkness of the eyelashes or clusters or discolorations on the surface of the eye or iris. This leads to a next stage of noise filtration where only larger sequential, continuous regions of dark pixels are identified, the largest of which is assumed to be the dark pupil.

At this point it is important to note that traditional advanced eye tracking that uses corneal reflection could be used to further define gaze direction. In this technology a byproduct of the infrared LED shown on the surface of the pupil is described in the prior art as a source of additional precision in the analysis of pupil position and location.

However, because the environment is sufficiently controlled in the desktop unit, this is not a necessary step. This is because one does not assume that the eye is moving significantly to the right or the left, and as a result one need not calculate gaze by cancelling out the effect of the head direction relative to the eye position. Instead, because the face mask fixes the head position toward the front, facing the screen, one can assume that the gaze is also in that direction and therefore one can skip the calculation of gaze utilizing corneal reflection. The circular shape of the ellipse that represents the dark pupil is then passed to a processing stage that applies an ellipse fit function onto the eye.

The state of processing for the desktop unit that calculates eye tracking parameters and variables off of two cameras and infrared lights shined onto the eye involves camera and infrared lights set up and configured on the front of the mask of the desktop eye tracking system.

After the dark pupil extreme positions are calculated, the algorithm finds the largest continuous region of ellipse parameterization and uses this as the estimated center point for the dark pupil. This dark pupil is then converted into a time stamp and dark pupil image data location, which is then passed to the next stage of the processing algorithm. The next stage of the processing algorithm takes the dark pupil data, runs the ellipse fit over it and uses the ellipse fit in order to generate the centroid of the ellipse in terms of x and y position as well as the time stamp, referred to herein as x, y and t for the names for the variables that are used in the algorithm and calculations. The pupil position is generated containing all of the x, y and t values for the frames and the centroids of the ellipses. Those are represented in a long table or vector, where each row of the table contains one triplet set of x, y and t for each eye for the left eye and the right eye. This means that there is an x, y pair for the left eye and an x, y pair for the right eye at a single time stamp shared across both. That time stamp refers to the two images, one that is the left eye and one that is the right eye.

The next stage is a data processing stage, which runs through the table of x and y positions and eliminates any points where the algorithm outputs suspicious results. For instance, if a blink occurred or if the eye tracker briefly lost track of the dark pupils of the left or the right eye or perhaps both eyes at the same time, the algorithm will cancel this out and insert nulls or no data, NA's or zeros in place of the data that previously was x and y data. In addition, simplification in calculation can be made assuming that the eyes do not move faster than a certain velocity in the frame rate the eye should not jump more than a certain amount in any given direction between consecutive frames. Thus if the eye is seen to move larger than an expected range, it is safe to say the algorithm or the inbound image contained a source of error or was corrupted, or that the user introduced some environmental error which overwhelmed the signal. In any of these events, the data is canceled out.

The resulting data post filtering is now a sequence of data points referring to x and y for the left eye and the right eye as well as a time stamp for the pairs. Thus the centroid of the dark pupil defines the gaze direction and it is this gaze direction which establishes lead and lag times as the dot moves on the screen. Note, filtration techniques of data files are described in the prior art.

The x, y, time stamp and optionally the height and width of the ellipse for each of the left and right eye data as reflected in a table is then converted and brought to the algorithmic processing stage where the eye data is assessed to determine whether it is considered valid and appropriate given the assumptions of the test taking environment. For instance, the left and the right eye should be roughly in the same position with respect to each other and that people will not be moving cross-eyed randomly.

It has been found, contrary to glint position measuring systems, that the accuracy in establishing gaze direction is significantly higher when the target, in this case the pupil, is large. It will be appreciated that the size or extent of the glint is two orders of magnitude smaller by area versus the pupil. Therefore assuming the same pixel density, the larger pupil feature centroid is computed with greater accuracy. This being the case one can achieve exceptional accuracy without glint tracking by detecting the centroid of the pupil.

More particularly, the number of pixels that define a glint can be as little as four, whereas the number of pixels which define a pupil can be orders of magnitude more. The subject system ignores the problem of the accuracy associated for instance four pixels and rather achieves a greater accuracy when considering the vast larger number of pixels associated with a pupil. Moreover, calculation of pupil position may be done in a number of different ways to reduce position error even further.

There are numbers of ways in which cognitive impairment can be measured through eye tracking, most notably in the lag time or lead time of the eye as its seeks to track moving dot 70, this lag time or lead time is referred to as anticipatory timing.

Not only are the lag time and lead times indicative of cognitive ability, variations in anticipatory timing is a sensitive measurement of cognitive ability.

The net result is that one can utilize any of the number of techniques to measure cognitive ability in terms of gaze direction measurement and all such cognitive ability measurements are within the scope of the present invention.

It will be noted that in a measurement system that utilizes the previously described enclosure, there is absolutely no need for calibration of the system and that one need not have a separate calculation for use by a test administrator precisely because no calibration is necessary.

Figure 5:
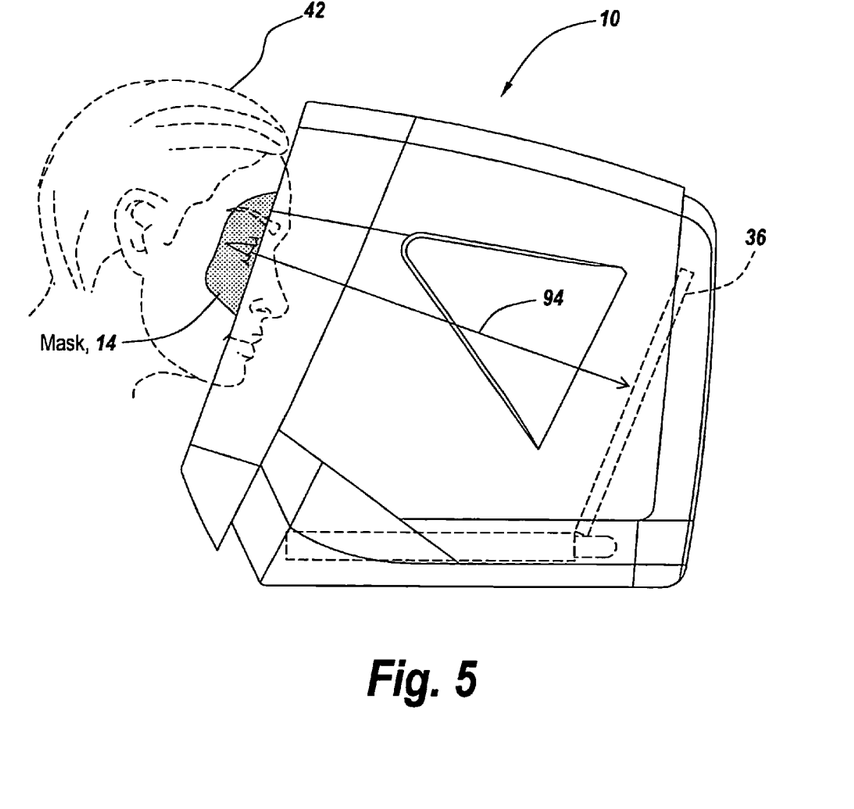
FIG. 5 is a diagrammatic illustration of the enclosure of FIG. 2 illustrating the distance between the eyes and the screen of the laptop contained within the enclosure.

Referring now to FIG. 5, it is noted that the distance of the eyes of individual 42 to screen 36 as illustrated by arrow 94 is to be no less than 38 centimeters and no more than 42 centimeters for the reasons discussed above. Thus, by pressing the individual's face to mask 14 all critical measurement parameters are established for accurate cognitive assessments.

Figure 6:
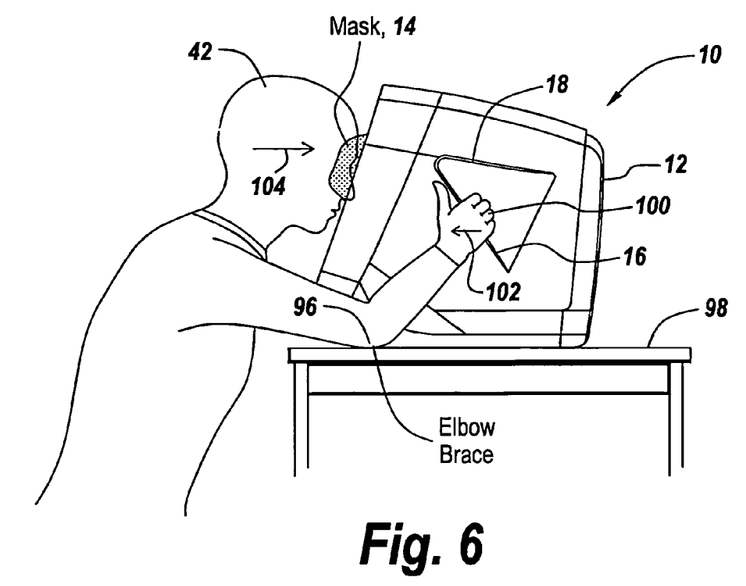
FIG. 6 is a diagrammatic illustration of the utilization of handholds to either side of the enclosure of FIG. 1 to permit the individual utilizing the machine to press his face against the mask, with the individual braced utilizing his elbows against a table on which the enclosure rests.

Referring now to FIG. 6, the ability of the individual 42 to position his face relative to mask 14 and keep it immobilized with respect to the enclosure is made easy through the utilization of handholds 16 and 18 on the exterior surface of enclosure 12. Here it can be seen that individual 42 has an elbow 96 placed on a table 98 which forms an elbow support such that when the individual's hand 100 grasping handhold 16 moves in the direction of arrow 102 the face of the individual 42 is moved in direction of arrow 104.

It will be appreciated that the accuracy of the subject system is critically due to the ability to immobilize the head the test taking individual, both with respect to the enclosure and mask and with respect therefore to the internally carried laptop computer screen or other screen of a computing device that is provided.

By providing an easy method for the individual taking the test to clamp his face to the mask one provides for accurate cognitive ability measurement with a desktop-based opto-cognitive device and system.

It will be noted that an individual seated in front of the subject desktop enclosure may have a tendency to move his or her head during a test that swings the test.

However, by providing an ergonomically designed enclosure, mask and handhold combination, the individually if seated in front of the enclosure can brace himself or herself utilizing the elbow based method illustrated in FIG. 6.

Figure 7:
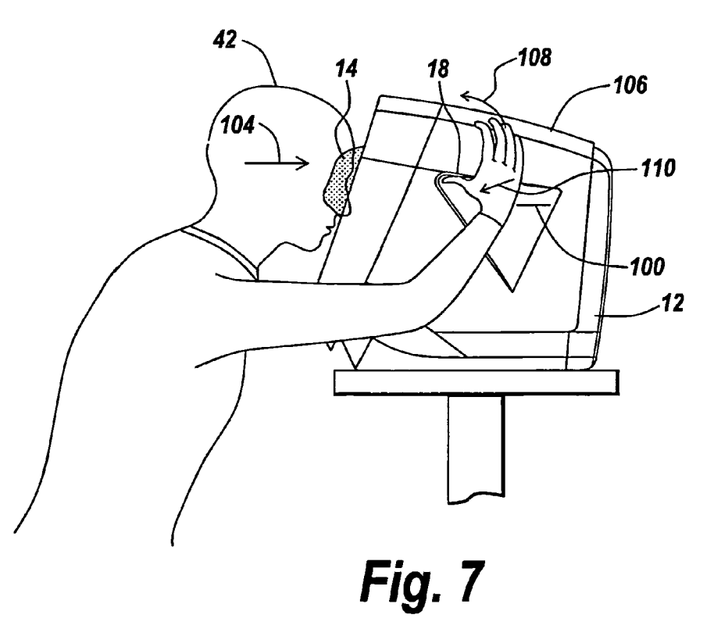
FIG. 7 is a diagrammatic illustration of the utilization of the handhold on the side of the subject enclosure in which the individual utilizing the machine can press his face to the mask with his hands gripping the handle by pushing upward inside the handhold with the thumb and grasping down the enclosure from the top with the other fingers to stabilize his face against the mask.

Referring to FIG. 7, if individual 42 is standing in front of the machine supported at eye height, the individual can nonetheless clamp his face to mask 14 utilizing handle 18 by wrapping the fingers of his hand 100 over the top portion 106 of enclosure 12 as illustrated by arrow 108. Here the individual clasps handhold 18 and moves his handhold in the direction of arrow 110 to move his head again as illustrated by arrow 104 towards mask 14. Since the individual does not have the ability to support his elbow as illustrated in FIG. 6, he can nonetheless take a test in a standing position with his face pressed to mask 14 through the gripping mechanism described in this figure.

Figure 8:
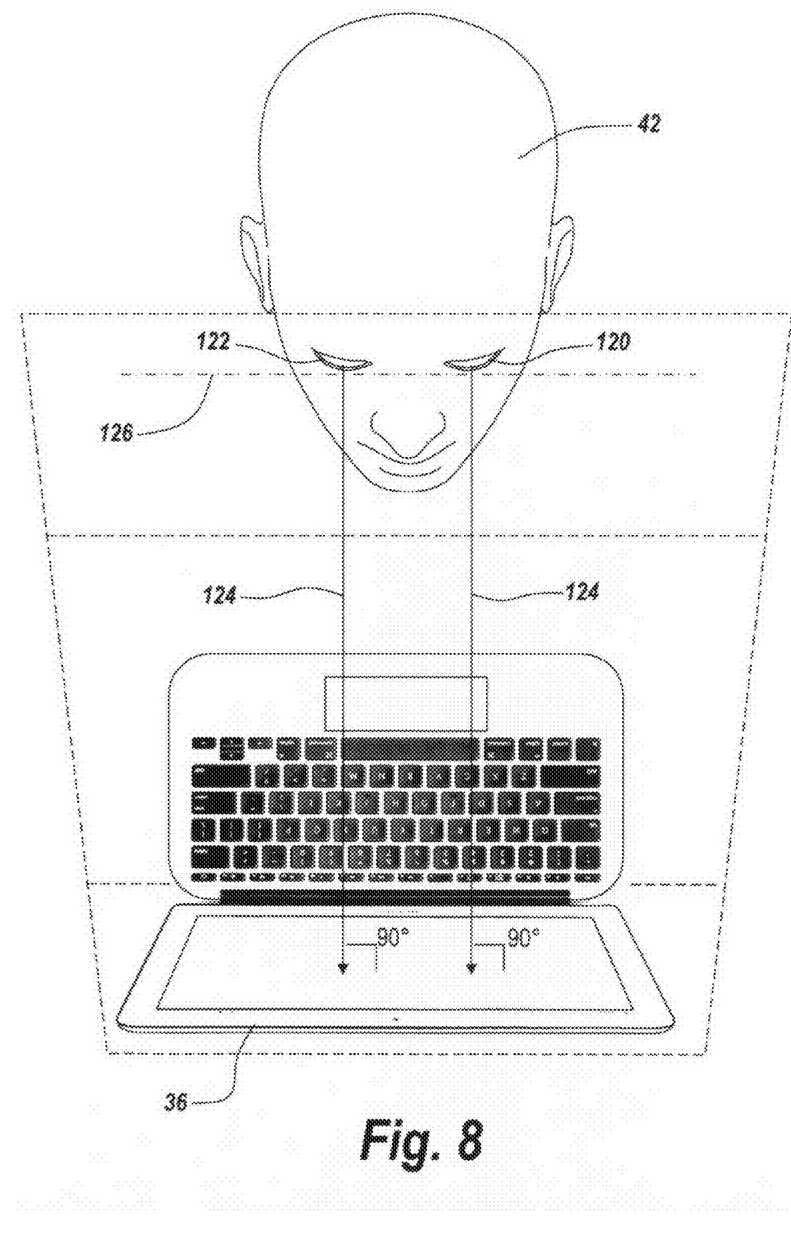
FIG. 8 is a diagrammatic illustration that the mask of FIGS. 1 through 7 maintains the line of sight from the eyes to the screen of the computing device housed inside the enclosure at 90 degrees to the plane of the screen, thereby to enable an accurate gaze direction measurement; and, FIG. 9 is a diagrammatic illustration of the clam shell type construction of one embodiment of the enclosure of FIG. 1, illustrating a computing device supported on the base of a lower clam shell, with the screen of the computing device being supported at the appropriate couple and orientation on ribs extending from the clam shell base, with the pivot point for the clam shells being sufficiently forward so as to minimize the space required for the device.

Referring now to FIG. 8, what is shown is that the eyes of individual 42, here shown at 120 and 122 have a line of sight direction illustrated at 124 that is orthogonal to the plane of computer screen 36 as illustrated by the 90-degree angles. It will be appreciated that when the head of individual 42 is clamped in the position illustrated in FIG. 8, the plane illustrated by dotted line 126 of eyes 120 and 122 is parallel to the plane of plane 36.

As mentioned before, the importance of such of arrangement is that no calibration is necessary to determine gaze direction due to the fixed placement of the individual's head with respect to the screen, with the sight lines normal to the screen.

Figure 9:
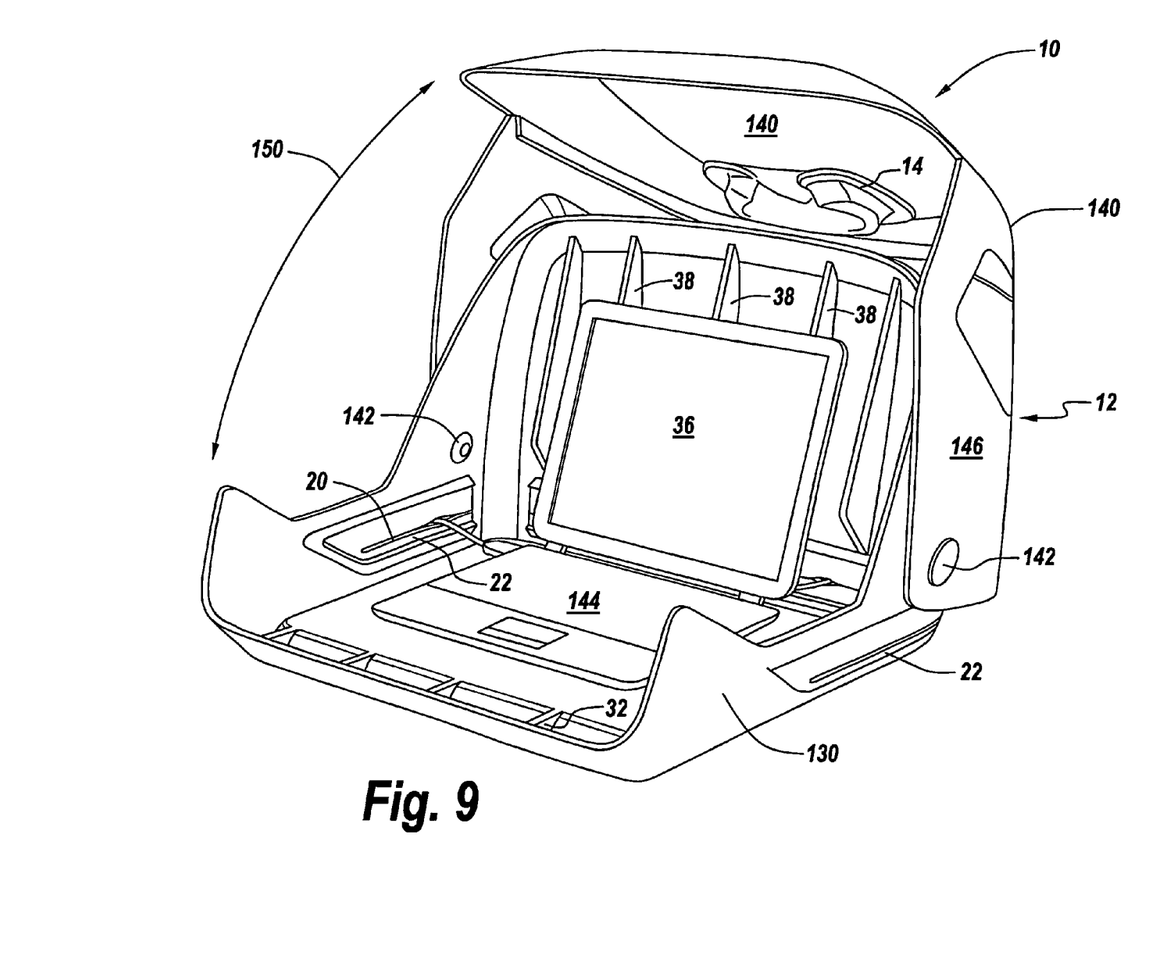

Referring to FIG. 9, in which like elements of FIGS. 2 and 9 have like reference characters, what can be seen is that in one embodiment the enclosure is a hinged clam shell enclosure having a bottom base 130 and a top clam shell portion 140 hinged together at hinge pin 142. Here a laptop having a base portion 32 and a hinged screen portion 36 are supported by the base ribs 32 as described hereinabove. Likewise the computer screen 36 of the laptop is supported by the aforementioned ribs 38 such that not only is the angle of the screen with respect to the laptop base maintained, the plane of the screen 36 is determined by the plane of ribs 38 such that its plane is referenced to the plane of face plate 146 of top clam shell 140 that carries mask 14. Here slit structure 20 permits passage of tables 22 through the enclosure as shown.

It will be seen that with this pivoted clam shell structure, a laptop or other computing device can be easily positioned within enclosure 12, with the position of the pivot point as well as the configuration of the sidewalls 146 of the upper clam shell minimizing the amount of area that is necessary for the support of the subject device such that when the clam shell is opened as illustrated by double ended arrow 150 there is sufficient clearance for a desktop device, without having to leave a large amount of space to permit the opening of the clam shell.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A desktop based opto-cognitive system for cognitive assessment comprising:
    an enclosure having a back plane and a front face plate with a mask therethrough adapted to receive an individual's face in a light tight fit and adapted to position the individual's face such that a normal to the individual's face is normal to the back plane of said enclosure;
    a computer screen positioned within said enclosure such that said computer screen is parallel to said back plane;
    an illumination device aimed at said mask and adapted to impinge on an eye of said individual when the face of said individual is pressed against said mask so as to illuminate said eye for contrasting the pupil of said eye as opposed to the white area of the eye of said individual;
    a camera within said enclosure, focused on said eye and having an output used to determine gaze direction; and,
    a processor coupled to said computer screen for presenting a moving object thereon, and coupled to the output of said camera for detecting gaze direction of said eye and for calculating cognitive ability based on the ability of said individual to track said moving object with said eye.

2. The system of claim 1, wherein said camera is a first camera of a plurality of cameras that includes a second camera trained on a different eye from said first camera.

3. The system of claim 1, wherein said illumination device includes a red LED.

4. The system of claim 3, wherein said red LED is located on said mask.

5. The system of claim 1, wherein said enclosure includes handles to either side of said enclosure, said handles adapted to be grasped by said individual so that said individual can clamp his head to said mask, thereby eliminating head movement with respect to said computer screen.

6. The system of claim 5, wherein said processor utilizes pupil tracking to ascertain gaze direction.

7. The system of claim 6, wherein said camera is a low cost camera having a resolution only sufficient to track said pupil.

8. The system of claim 1, wherein said enclosure includes a clam shell enclosure having a rear hinge adapted to permit the opening of said clam shell enclosure, said clam shell enclosure having a top portion carrying said mask and a bottom portion adapted to receive said computer screen.

9. The system of claim 8, wherein said bottom portion has a number of ribs extending from said back plane for orienting said computer screen with respect to said bottom portion such that when said clam shell is closed a sight line from the eyes of said individual to said computer screen is at a right angle to the surface of said computer screen.

10. The system of claim 9, wherein said computer screen is part of a laptop computer and wherein said laptop computer is located on the bottom portion of said clam shell.

11. The system of claim 1, wherein said gaze direction is utilized to calculate cognitive impairment.

12. The system of claim 11, wherein calculating said cognitive impairment includes measurement of lag time or lead time that said eye takes to track said moving object.

13. The system of claim 12, wherein calculating said cognitive impairment includes measuring regularity in the variation of said lag time or lead time.

14. A method of portable measurement of cognitive abilities of an individual comprising:
providing a light tight enclosure having a mask at a front face thereto adapted to receive the face of an individual;
providing a computer screen within said enclosure and spaced from the mask;
driving the computer screen so as to present a moving object;
providing a camera adapted to be trained on an eye of the individual when the face of the individual is pressed to said mask;
illuminating the eye of the individual;
processing an output of the camera to establish gaze direction by determining the location of the pupil of the individual when the individual presses his face against the mask to prevent head movement relative to the computer screen and the individual seeks to track the moving object on the computer screen; and
calculating cognitive ability of the individual based on the ability of the individual to track the moving object with said eye.

15. The method of claim 14, wherein the mask constrains the face of the individual such that a sight line from the eyes of the individual to the computer screen is orthogonal to the plane of the computer screen.

16. The method of claim 15, wherein the computer screen is spaced from the eyes of the individual by between 38 to 42 centimeters.

17. The method of claim 14, wherein the mask is made from a noncompressible yet comfortable foam material.

18. The method of claim 17, wherein the foam material has a 55 shore hardness.

19. The method of claim 18, wherein the mask is a universal mask capable of fitting any adult face so as to provide a fixed distance between the eyes of the individual and the computer screen.

20. The method of claim 19, wherein the portion of the mask that engages the cheek bones of the individual is sized to provide enough depth within the enclosure, in front of the individual's eyes, to accommodate a light source for illumination of the individual's eye.

* * * * *